(12) United States Patent
Enoki et al.

(10) Patent No.: US 7,056,671 B2
(45) Date of Patent: Jun. 6, 2006

(54) ISOTHERMAL CHIMERIC PRIMER NUCLEIC ACID AMPLIFICATION METHODS USING BLOCKING OGLIONUCLEOTIDE

(75) Inventors: Tatsuji Enoki, Shiga (JP); Hiroaki Sagawa, Shiga (JP); Ikunoshin Kato, Shiga (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 10/486,645

(22) PCT Filed: Aug. 20, 2002

(86) PCT No.: PCT/JP02/08357

§ 371 (c)(1),
(2), (4) Date: Feb. 12, 2004

(87) PCT Pub. No.: WO03/016569

PCT Pub. Date: Feb. 27, 2003

(65) Prior Publication Data

US 2005/0059003 A1    Mar. 17, 2005

(30) Foreign Application Priority Data

Aug. 20, 2001  (JP) ............................. 2001-249497

(51) Int. Cl.
*C12Q 1/68*  (2006.01)
*C12P 19/34*  (2006.01)

(52) U.S. Cl. .................. 435/6; 435/91.1; 435/91.2
(58) Field of Classification Search ................ 435/91.2
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,957,858 A | 9/1990 | Chu et al. |
| 5,364,760 A | 11/1994 | Chu et al. |
| 5,409,818 A | 4/1995 | Davey et al. |
| 5,455,166 A | 10/1995 | Walker |
| 5,554,517 A | 9/1996 | Davey et al. |
| 5,744,308 A | 4/1998 | Guillou-Bonnici et al. |
| 5,824,517 A | 10/1998 | Cleuziat et al. |
| 5,916,777 A | 6/1999 | Kacian et al. |
| 6,063,603 A | 5/2000 | Davey et al. |
| 6,087,133 A | 7/2000 | Dattagupta et al. |
| 6,214,587 B1 | 4/2001 | Dattagupta et al. |
| 6,251,639 B1 * | 6/2001 | Kurn ........................ 435/91.2 |
| 6,410,278 B1 | 6/2002 | Notomi et al. |
| 6,423,495 B1 | 7/2002 | Oultram et al. |
| 2002/0168676 A1 | 11/2002 | Notomi et al |
| 2003/0073081 A1 | 4/2003 | Mukai et al |

FOREIGN PATENT DOCUMENTS

| | | |
|---|---|---|
| EP | 0 320 308 B1 | 6/1989 |
| JP | 07 114718 | 5/1995 |
| WO | WO 95/25180 | 9/1995 |
| WO | WO 99/09211 | 2/1999 |
| WO | WO 99/49081 A2 | 9/1999 |
| WO | WO 00/28082 | 5/2000 |
| WO | WO 00/56877 | 5/2000 |
| WO | WO 01/20035 A2 | 3/2001 |
| WO | WO 02/16639 | 2/2002 |
| WO | WO 02/18616 A1 | 3/2002 |
| WO | WO0218616 A1 * | 3/2002 |

OTHER PUBLICATIONS

Larrick, J.W., "Message Amplification Phenotyping (MAPPing)*—Principles, Practice and Potential", Trends in Biotechnology. May. 1992, vol. 10, No. 5. 146-152.

"Recent Advances in PCR Methodology: Basic Methodology and it's Application", Protein, Nucleic Acid and Enzyme, Supplement. Apr. 1996. vol. 41, No. 5, 425-428.

Gingeras, et al., *PCR Protocols, A guide to methods and applications*: "A Transcription-Based Amplification System Chp. 30", INNIS, et al. Ed., Academic Press Inc. 1990. San Diego, Chapter 30, 245-252.

Fu, Dong-Jing, "Sequencing Double-Stranded DNA By Strand Displacement", Nucleic Acids Research, Oxford University Press, Surrey, GB, (1997), pp. 677-679, vol. 25, No. 3, XP000196977, ISSN: 0305-1048.

* cited by examiner

*Primary Examiner*—Kenneth A. Horlick
*Assistant Examiner*—Christopher M. Babic
(74) *Attorney, Agent, or Firm*—Browdy and Neimark, PLLC (57) ABSTRACT

Methods of amplifying a target nucleic acid whereby the target nucleic acid is amplified in the presence of a deoxyribonucleotide triphosphate, a DNA polymerase having strand displacement activity, at least one chimeric oligonucleotide primer, at least one upstream block oligonucleotide and a RNase H; wherein the chimeric oligonucleotide primer contains a ribonucleotide positioned at the 3'-terminus; wherein the upstream block oligonucleotide is capable of annealing to a region 3' to a portion in the nucleic acid as the template to which the chimeric oligonucleotide primer anneals; and compositions and kits thereof.

6 Claims, 1 Drawing Sheet

Figure 1

ISOTHERMAL CHIMERIC PRIMER NUCLEIC ACID AMPLIFICATION METHODS USING BLOCKING OGLIONUCLEOTIDE

TECHNICAL FIELD

The present invention relates to a method for detecting a target nucleic acid which is useful in a field of clinical medicine and a DNA synthesis method which is useful in a field of genetic engineering. The present invention relates to a method for amplifying a nucleic acid as a template and a method for detecting a target nucleic acid amplified using said method.

BACKGROUND ART

DNA synthesis is used for various purposes in studies in a field of genetic engineering. Most of the DNA synthesis with the exception of that of a short-chain DNA (e.g., an oligonucleotide) is carried out using an enzymatic method in which a DNA polymerase is utilized. An exemplary method is the polymerase chain reaction (PCR) method as described in U.S. Pat. Nos. 4,683,195, 4,683,202 and 4,800,159 in detail. Another example is the reverse transcription-PCR (RT-PCR) method, which is a combination of the PCR and a reverse transcriptase reaction, as described in Trends in Biotechnology, 10:146–152 (1992). The development of the above-mentioned methods has enabled the amplification of a region of interest from a DNA or an RNA.

The above-mentioned DNA synthesis methods are conducted, for example, using a reaction that consists of three steps. The three steps are a step of dissociating (denaturing) a double-stranded DNA as a template into single-stranded DNAs, a step of annealing a primer to the single-stranded DNA and a step of synthesizing (extending) a complementary strand from the primer in order to amplify a region of a DNA of interest. Alternatively, they are conducted using a reaction designated as "the shuttle PCR" ("PCR hou saizensen" (Recent advances in PCR methodology), Tanpakushitsu Kakusan Kouso, Bessatsu, (Protein, Nucleic Acid and Enzyme, Supplement), 41(5):425–428 (1996)) in which two of the three steps, that is, the step of annealing the primer and the step of extending are carried out at the same temperature.

Alternatively, the ligase chain reaction (LCR) method as described in EP 320,308 published on Jun. 14, 1989 or the transcription-based amplification system (TAS) method as described in PCR Protocols, Academic Press Inc., 1990, pp. 245–252 may be used. The four methods as mentioned above require repeating a reaction at a high temperature and that at a low temperature several times in order to regenerate a single-stranded target molecule for the next amplification cycle. The reaction system should be conducted using discontinuous phases or cycles because the reaction is restricted by the temperatures as described above.

Thus, the methods require the use of an expensive thermal cycler that can strictly adjust a wide range of temperatures over time. Furthermore, the reaction requires time for adjusting the temperature to the two or three predetermined ones. The loss of time increases in proportion to the cycle number.

Nucleic acid amplification methods that can be carried out isothermally have been developed in order to solve the problems. Examples thereof include the strand displacement amplification (SDA) method as described in JP-B 7-114718, the self-sustained sequence replication (3SR) method, the nucleic acid sequence based amplification (NASBA) method as described in Japanese Patent No. 2650159, the transcription-mediated amplification (TMA) method, the Qβ replicase method as described in Japanese Patent No. 2710159 and the various modified SDA methods as described in U.S. Pat. No. 5,824,517, WO 99/09211, WO 95/25180 and WO 99/49081. A method of isothermal enzymatic synthesis of an oligonucleotide is described in U.S. Pat. No. 5,916,777. Extension from a primer and/or annealing of a primer to a single-stranded extension product (or to an original target sequence) followed by extension from the primer take place in parallel in a reaction mixture incubated at a constant temperature in the reaction of such a method of isothermal nucleic acid amplification or oligonucleotide synthesis.

Among the isothermal nucleic acid amplification methods, the SDA method is an example of systems in which a DNA is finally amplified. The SDA method is a method for amplifying a target nucleic acid sequence (and a complementary strand thereof) in a sample by displacement of double strands using a DNA polymerase and a restriction endonuclease. The method requires four primers used for the amplification, two of which should be designed to contain a recognition site for the restriction endonuclease. The method requires the use of a modified deoxyribonucleotide triphosphate as a substrate for DNA synthesis in large quantities. An example of the modified deoxyribonucleotide triphosphates is an (α-S) deoxyribonucleotide triphosphate in which the oxygen atom of the phosphate group at the α-position is replaced by a sulfur atom (S). The problem of running cost associated with the use of the modified deoxyribonucleotide triphosphate becomes serious if the reaction is routinely conducted, for example, for genetic test. Furthermore, the incorporation of the modified nucleotide (e.g., the (α-S) deoxyribonucleotide) into the amplified DNA fragment in the method may abolish the cleavability of the amplified DNA fragment with a restriction enzyme, for example, when it is subjected to a restriction enzyme fragment length polymorphism (RFLP) analysis.

The modified SDA method as described in U.S. Pat. No. 5,824,517 is a DNA amplification method that uses a chimeric primer that is composed of an RNA and a DNA and has, as an essential element, a structure in which DNA is positioned at least at the 3' terminus. The modified SDA method as described in WO 99/09211 requires the use of a restriction enzyme that generates a 3'-protruding end. The modified SDA method as described in WO 95/25180 requires the use of at least two pairs of primers. The modified SDA method as described in WO 99/49081 requires the use of at least two pairs of primers and at least one modified deoxyribonucleotide triphosphate. On the other hand, the method for synthesizing an oligonucleotide as described in U.S. Pat. No. 5,916,777 comprises synthesizing a DNA using a primer having a ribonucleotide at the 3' terminus, completing a reaction using the primer, introducing a nick between the primer and an extended strand in an primer-extended strand with an endonuclease to separate them from each other, digesting a template and recovering the primer to reuse it. It is required to isolate the primer from the reaction system and then anneal it to the template again in order to reuse the primer in the method. Additionally, the Loop-mediated Isothermal Amplification (LAMP) method as described in WO 00/28082 requires four primers for amplification and the products amplified using the method are DNAs having varying size in which the target regions for the amplification are repeated.

Furthermore, an isothermal nucleic acid amplification method using a chimeric oligonucleotide primer, Isothermal and Chimeric primer-initiated Amplification of Nucleic acids (ICAN) method, as described in WO 00/56877 or WO 02/16639 is known. However, the conventional isothermal nucleic acid amplification methods still have various problems. Thus, a method for amplifying a nucleic acid at low running cost by which a DNA fragment that can be further genetically engineered is obtained has been desired.

OBJECTS OF INVENTION

The main object of the present invention is to provide a target nucleic acid amplification method in which a target nucleic acid in a sample is specifically amplified with a high sensitivity, as well as a composition and a kit used for the method.

SUMMARY OF INVENTION

As a result of intensive studies, the present inventors have found that an efficiency of target nucleic acid amplification is increased and a detection sensitivity is improved by using a combination of a chimeric oligonucleotide primer and an upstream block oligonucleotide that anneals to a portion 3' to a portion in a nucleic acid as a template to which the primer anneals in the ICAN method as described in WO. 00/56877 or WO 02/16639. Thus, the present invention has been completed.

The first aspect of the present invention relates to a method for amplifying a nucleic acid, the method comprising:
  (a) preparing a reaction mixture by mixing a nucleic acid as a template, a deoxyribonucleotide triphosphate, a DNA polymerase having a strand displacement activity, at least one chimeric oligonucleotide primer, at least one upstream block oligonucleotide and an RNase H,
  wherein the chimeric oligonucleotide primer is a chimeric oligonucleotide primer that is substantially complementary to the nucleotide sequence of the nucleic acid as the template and contains a ribonucleotide as well as at least one selected from the group consisting of a deoxyribonucleotide and a nucleotide analog, the ribonucleotide being positioned at the 3' terminus or on the 3'-terminal side of the primer, and
  wherein the upstream block oligonucleotide is substantially complementary to a nucleotide sequence 3' to a region in the nucleic acid as the template that is substantially complementary to the chimeric oligonucleotide primer, and the nucleotide at the 3' terminus of the upstream block oligonucleotide is modified such that a reaction of complementary strand extension by the action of the DNA polymerase does not take place; and
  (b) incubating the reaction mixture for a sufficient time to generate a reaction product.

According to the first aspect, the reaction mixture may further contain a second chimeric oligonucleotide primer having a sequence substantially homologous to the nucleotide sequence of the nucleic acid as the template. The reaction mixture may further contain an upstream block oligonucleotide that has a sequence substantially homologous to a nucleotide sequence 5' to a region in the nucleic acid as the template that has a sequence substantially homologous to the nucleotide sequence of the second chimeric oligonucleotide primer, and the nucleotide at the 3' terminus of the upstream block oligonucleotide is modified such that a reaction of complementary strand extension by the action of the DNA polymerase does not take place.

The second aspect of the present invention relates to a composition for the method for amplifying a nucleic acid of the first aspect, which contains at least one chimeric oligonucleotide primer and at least one upstream block oligonucleotide.

The third aspect of the present invention relates to a kit for the method for amplifying a nucleic acid of the first aspect, which contains at least one chimeric oligonucleotide primer and at least one upstream block oligonucleotide.

The fourth aspect of the present invention relates to a method for detecting a target nucleic acid, the method comprising:
  (a) amplifying a target nucleic acid by the method for amplifying a nucleic acid of the first aspect; and
  (b) detecting a target nucleic acid amplified in the previous step.

DETAILED DESCRIPTION OF THE INVENTION

Figure 1:
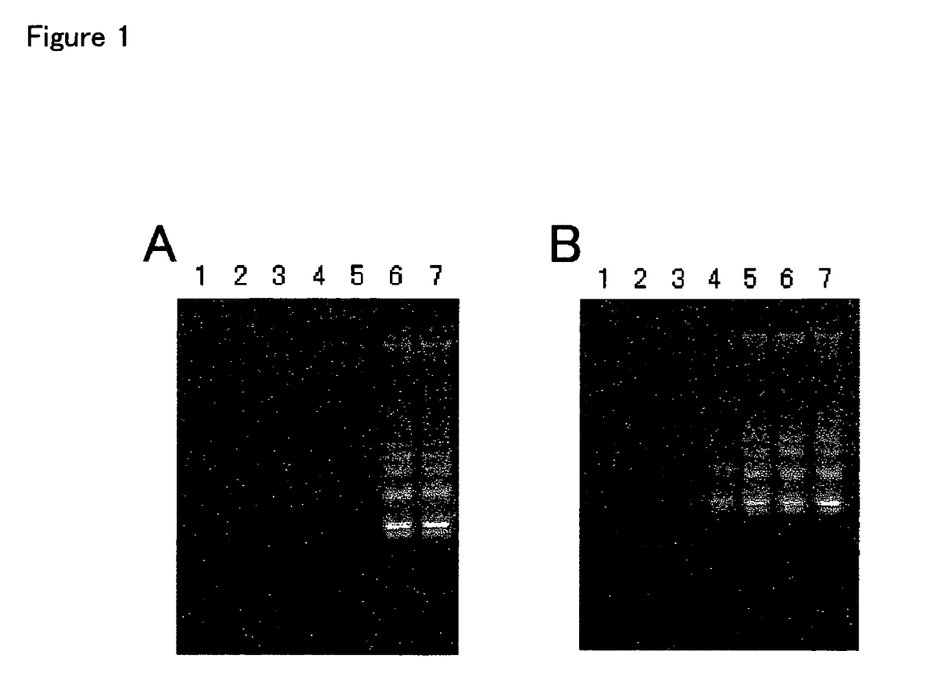
FIG. 1: a figure that represents the results of agarose gel electrophoresis of DNA fragments amplified according to the method of the present invention.

As used herein, a deoxyribonucleotide (also referred to as a dN) refers to a nucleotide of which the sugar portion is composed of D-2-deoxyribose. The deoxyribonucleotides include, for example, ones having adenine, cytosine, guanine or thymine as the base portion. Furthermore, the deoxyribonucleotides also include a deoxyribonucleotide having a modified base such as 7-deazaguanosine and a deoxyribonucleotide analog such as deoxyinosine nucleotide.

As used herein, a ribonucleotide (also referred to as an N) refers to a nucleotide of which the sugar portion is composed of D-ribose. The ribonucleotides include ones having adenine, cytosine, guanine or uracil as the base portion. The ribonucleotides also include modified ribonucleotides such as a modified ribonucleotide in which the oxygen atom of the phosphate group at the α-position is replaced by a sulfur atom (also referred to as an (α-S) ribonucleotide or an (α-S) N) or other derivatives.

The chimeric oligonucleotide primers used in the present invention include any chimeric oligonucleotide primer that has a ribonucleotide being positioned at the 3' terminus or on the 3'-terminal side of the primer, can be used to extend a nucleic acid strand in the method of the present invention, can be cleaved with an endonuclease, and can be used to effect a strand displacement reaction.

As used herein, 3'-terminal side refers to a portion from the center to the 3' terminus of a nucleic acid such as a primer. Likewise, 5'-terminal side refers to a portion from the center to the 5' terminus of a nucleic acid.

As used herein, an upstream portion refers to an arbitrary portion that is 5' to the 5' terminus of the chimeric oligonucleotide primer to be used in the method of the present invention. In other words, it is an arbitrary portion that is 3' to the primer in a strand of a nucleic acid as a template to which the chimeric oligonucleotide primer anneals.

As used herein, an endonuclease may be any one that acts on a double-stranded DNA generated by extending a DNA from the chimeric oligonucleotide primer which have been annealed to a nucleic acid as a template, and specifically cleaves it at a portion of the primer that contains a ribonucleotide.

As used herein, a DNA polymerase refers to an enzyme that synthesizes a DNA strand de novo using a DNA strand as a template. The DNA polymerases include naturally occurring DNA polymerases and variant enzymes having the above-mentioned activity. For example, such enzymes include a DNA polymerase having a strand displacement activity, a DNA polymerase lacking a 5'→3' exonuclease activity and a DNA polymerase having a reverse transcriptase activity or an endonuclease activity.

As used herein, "a strand displacement activity" refers to an activity that can effect a strand displacement, that is, that can proceed DNA duplication on the basis of the sequence of the nucleic acid as the template while displacing the DNA strand to release the complementary strand that has been annealed to the template strand. In addition, a DNA strand released from a nucleic acid as a template as a result of a strand displacement is referred. to as "a displaced strand" herein.

Hereinafter, the present invention will be described in detail.

(1) Chimeric Oligonucleotide Primer Used in the Present Invention

The primer used in the method of the present invention is a chimeric oligonucleotide primer that contains a ribonucleotide as well as at least one selected from the group consisting of a deoxyribonucleotide and a nucleotide analog. Such primers also include an oligoribonucleotide primer that contains an unmodified ribonucleotide and/or a modified ribonucleotide.

A chimeric oligonucleotide primer used in the method of the present invention is a chimeric oligonucleotide primer that has a nucleotide sequence substantially complementary to a part of the nucleotide sequence of a nucleic acid as a template. It can contribute to extension of a DNA strand under conditions used. Furthermore, a ribonucleotide is positioned at the 3' terminus or on the 3'-terminal side of the chimeric oligonucleotide primer. The primer is usually designed such that it is complementary to a portion upstream of the region to be amplified, that is, a portion 3' to the nucleotide sequence corresponding to a region to be amplified in a nucleic acid as a template. As used herein, "a substantially complementary nucleotide sequence" means a nucleotide sequence that can anneal to a DNA as a template under reaction conditions used.

The chimeric oligonucleotide primer used in the method of the present invention may contain one or more modified ribonucleotide. As used herein, a ribonucleotide may be an unmodified ribonucleotide and/or a modified ribonucleotide that can be positioned at the 3' terminus or on the 3'-terminal side of a chimeric oligonucleotide primer and that is recognized by or cleaved with an endonuclease. The ribonucleotides include both of the unmodified ribonucleotide and the modified ribonucleotide as described above. An unmodified ribonucleotide, a modified ribonucleotide or a combination thereof can be used for the chimeric oligonucleotide primer of the present invention as long as it does not abolish the function of the primer. Examples of the modified ribonucleotides include, but are not limited to, an ($\alpha$-S) ribonucleotide in which the oxygen atom bound to the phosphate group is replaced by a sulfur atom, and a ribonucleotide in which the hydroxy group at the 2-position of the ribose is replaced by a methoxy group. Such a chimeric oligonucleotide primer containing a modified ribonucleotide can be produced by using, for example, an ($\alpha$-S) ribonucleotide triphosphate, which is prepared by a method using a sulfuration reaction reagent (Glen Research) as described in U.S. Pat. No. 5,003,097, or a 2-OMe-RNA-CE phosphoramidite reagent (Glen Research).

A chimeric oligonucleotide primer that can be used in the amplification method of the present invention may be designed to contain a modified ribonucleotide that confers resistance to the cleavage with an endonuclease. Such a primer is useful in that one can control the cleavage site with an endonuclease during amplification reaction steps.

One or two chimeric oligonucleotide primers may be used in the method of the present invention depending on the desired form of a DNA fragment after amplification (single-stranded or double-stranded). Specifically, one chimeric oligonucleotide primer is used when a single-stranded DNA is desired, whereas two primers are used when a double-stranded DNA is desired.

There is no specific limitation concerning the length of the chimeric oligonucleotide primer used according to the present invention as long as it has a ribonucleotide at the 3' terminus or on the 3'-terminal side and it can be used for the ICAN method.

The length of the chimeric oligonucleotide primer that can be used is, for example, about 6 nucleotides to about 100 nucleotides, preferably about 10 nucleotides to about 50 nucleotides, more preferably about 12 nucleotides to about 40 nucleotides. It is preferable that the nucleotide sequence of the chimeric oligonucleotide is substantially complementary to a nucleic acid as a template such that it anneals to the nucleic acid as the template under reaction conditions used. The primer contains a sequence recognized by an endonuclease, which is utilized in a step as described below, at the 3' terminus or on the 3'-terminal side.

For example, an oligonucleotide having a structure represented by the following general formula can be used in the DNA synthesis method of the present invention as a primer, although it is not intended to limit the present invention:

General formula: 5'-dNa-Nb-dNc-3'

(dN: deoxyribonucleotide and/or nucleotide analog; N: unmodified ribonucleotide and/or modified ribonucleotide, wherein some of dNs in dNa may be replaced by Ns, and the nucleotide at the 3' terminus may be modified such that extension from the 3' terminus by the action of the DNA polymerase does not take place).

In the above-mentioned general formula, a is, for example, an integer of 5 or more, preferably 6 or more, more preferably 8 or more; b is an integer of 1 or more, for example, 1–15, preferably 1–10, more preferably 1–7, most preferably 1–5; and c may be 0 or c may be an integer of 1 or more, preferably 0–5, more preferably 0–3, although it is not intended to limit the present invention.

Although it is not intended to limit the present invention, examples of chimeric oligonucleotide primers used according to the present invention include ones in which a=8; and b=1 and c=0, b=2 and c=0, b=3–5 and c=0, or b=2–3 and c=0–3. The numbers for a, b and c may be adjusted such that the chimeric oligonucleotide primer can be used in the method of the present invention.

The chimeric oligonucleotide primer used according to the present invention has a structure in which an endonuclease recognizes or cleaves a DNA strand extended from the primer by the action of a DNA polymerase (a primer-extended strand) at a site that contains a ribonucleotide, which ribonucleotide being positioned at the 3' terminus or on the 3'-terminal side of the chimeric oligonucleotide primer. Although it is not intended to limit the present invention, for example, when an RNase H acts on a double-stranded DNA generated by extending a DNA from a chimeric oligonucleotide primer represented by the general formula that has been annealed to a nucleic acid as a template, the chimeric oligonucleotide primer is cleaved at the ribonucleotide portion. A double-stranded DNA in which a nick is introduced between the oligonucleotide primer and the DNA strand synthesized by the extension is then generated. Then, a strand displacement reaction with a DNA polymerase proceeds from the nicked site. Thus, any chimeric oligonucleotide primer that can be used to extend a nucleic acid strand from the 3' terminus of the primer, that can be cleaved with an endonuclease, and with which a DNA polymerase can effect a strand displacement reaction can be used in the method of the present invention. Furthermore, the chimeric oligonucleotide primers of the present invention include one whose 3' terminus is modified such that extension by the action of the DNA polymerase cannot take place, and DNA extension takes place from a 3' terminus generated upon cleavage by the endonuclease.

In addition, a promoter sequence for an RNA polymerase may be included on the 5'-terminal side of the chimeric oligonucleotide primer. Such RNA polymerases are exemplified by T7 RNA polymerase and SP6 RNA polymerase.

Furthermore, the chimeric oligonucleotide primer used in the method of the present invention may contain a nucleotide analog or other substances. That is, one or more nucleotide analog(s) can be contained in the chimeric oligonucleotide primer of the present invention as long as the function of the primer for effecting a polymerase extension reaction from the 3' terminus by the action of a DNA polymerase is not abolished. Plural types of the nucleotide analogs can be used in combination. Examples of the nucleotide analogs include, but are not limited to, deoxyinosine nucleotide, deoxyuracil nucleotide, a nucleotide analog having a modified base such as 7-deazaguanine, a nucleotide analog having a ribose derivative and the like. Furthermore, the chimeric oligonucleotides used in the present invention may contain deoxynucleotides, ribonucleotides or nucleotide analogs having various modifications such as addition of labeled compounds as long as they retain the functions as described above.

Incorporation of a nucleotide analog into a primer is effective for suppressing the formation of high-order structure of the primer itself and stabilization of annealing formation with the template. A ribonucleotide may be incorporated into a primer for the same purpose. Although it is not intended to limit the present invention, a modified ribonucleotide such as (α-S) ribonucleotide can be preferably used in order to prevent the digestion of the primer by a non-specific endonuclease (RNase).

The chimeric oligonucleotide primer can be synthesized to have desired nucleotide sequence using, for example, the 394 type DNA synthesizer from Applied Biosystems Inc. (ABI) according to a phosphoramidite method. Alternatively, any methods including a phosphate triester method, an H-phosphonate method and a thiophosphonate method may be used to synthesize the chimeric oligonucleotide primer.

(2) Upstream Block Oligonucleotide Used According to the Present Invention

At least one selected from the group consisting of a deoxyribonucleotide and a nucleotide analog can be preferably used for an upstream block oligonucleotide used in the method of the present invention.

An upstream block oligonucleotide that has a nucleotide sequence substantially complementary to a portion of the nucleotide sequence of the nucleic acid as the template, and is capable of annealing to a region 3' to a portion in a nucleic acid as a template to which the chimeric oligonucleotide primer as described in (1) above anneals can be preferably used in the method of the present invention. The oligonucleotide is usually designed such that it is complementary to a portion upstream of the region to be amplified, i.e., a portion 3' to the nucleotide sequence corresponding to the region of the nucleic acid as the template to be amplified. As used herein, a "substantially complementary nucleotide sequence" means a nucleotide sequence that is capable of annealing to a DNA as a template under reaction conditions used.

As described above, the upstream block oligonucleotide according to the present invention is modified at the 3' terminus such that it cannot be utilized for a DNA extension reaction by the action of a DNA polymerase. There is no specific limitation concerning the means of modification as long as the above-mentioned objects can be achieved. Examples thereof include addition, at the 3' terminus, of a dideoxy nucleotide, a nucleotide modified at the hydroxyl group at the 3-position of ribose, or a nucleotide with modification that interferes with extension by a DNA polymerase due to steric hindrance. Alkylation or other known modification methods can be utilized for modification of the hydroxyl group at the 3-position of ribose of the upstream block oligonucleotide. For example, a DNA extension reaction can be prevented by aminoalkylation.

One or two upstream block oligonucleotide may be used in the method of the present invention depending on the desired form of a DNA fragment after amplification (single-stranded or double-stranded). Specifically, one chimeric oligonucleotide primer and one upstream block oligonucleotide are used when a single-stranded DNA is desired, whereas two chimeric oligonucleotide primers and two upstream block oligonucleotides are used when a double-stranded DNA is desired.

There is no specific limitation concerning the portion in a nucleic acid as a template to which the upstream block oligonucleotide used in the method of the present invention anneals as long as the selection of the portion results in the maximal amplification efficiency which may vary depending on the nucleotide sequence of the target nucleic acid, the length of the region to be amplified, and the portion in the target nucleic acid to which the chimeric oligonucleotide primer used in combination anneals. For example, the portion is selected such that the 3' terminus is located at a distance of one nucleotide or more from the 5' terminus of the chimeric oligonucleotide primer.

The preferable chain length of the upstream block oligonucleotide used in the method of the present invention may be any one as long as an effect of increasing sensitivity of detecting an amplified fragment of interest or the like is achieved.

Although it is not intended to limit the present invention, the length of the upstream block oligonucleotide is, for example, about 6 nucleotides to about 100 nucleotides, preferably about 10 nucleotides to about 50 nucleotides, more preferably about 12 nucleotides to about 40 nucleotides. It is preferable that the nucleotide sequence of the upstream block oligonucleotide is substantially complementary to a nucleic acid as a template such that it anneals to the nucleic acid as the template under reaction conditions used.

The upstream block oligonucleotide used in the method of the present invention may contain a nucleotide analog or other substances. The upstream block oligonucleotide according to the present invention may contain one or more nucleotide analogs. Plural kinds of nucleotide analogs can be used in combination. Although it is not intended to limit the present invention, a nucleotide analog that can be used according to the present invention is exemplified by deoxyinosine nucleotide, deoxyuracil nucleotide or a nucleotide analog having a modified base such as 7-deazaguanine, or a nucleotide analog having a ribose derivative. The upstream block oligonucleotide used in the present invention may contain a deoxynucleotide, ribonucleotide or a nucleotide analog having various modifications (e.g., addition of a labeled compound).

Incorporation of a nucleotide analog into the block oligonucleotide is effective for suppressing the formation of high-order structure of the oligonucleotide itself and stabilization of annealing formation with the template.

The upstream block oligonucleotide can be synthesized to have desired nucleotide sequence using, for example, the 394 type DNA synthesizer from Applied Biosystems Inc. (ABI) according to a phosphoramidite method. Alternatively, any methods including a phosphate triester method, an H-phosphonate method and a thiophosphonate method may be used to synthesize the upstream block oligonucleotide.

(3) Endonuclease Used in the Present Invention

Any endonuclease that can act on a double-stranded DNA generated by DNA extension from the chimeric oligonucleotide primer as described in (1) above that has been annealed to a nucleic acid as a template and cleaves the extended strand to effect a strand displacement reaction may be used in the present invention. That is, the endonuclease is an enzyme that can generate a nick in the chimeric oligonucleotide primer portion of the double-stranded DNA. Examples of endonucleases that can be used in the present invention include, but are not limited to, ribonucleases. Among these, endoribonuclease H (RNase H) which acts on an RNA portion of a double-stranded nucleic acid composed of a DNA and an RNA can be preferably used. Any ribonuclease that has the above-mentioned activities can be preferably used in the present invention, including mesophilic and heat-resistant ones. For example, an RNase H from *E. coli* can be used for a reaction at about 50° C. to about 70° C. in the method of the present invention. A heat-resistant ribonuclease can be preferably used in the method of the present invention. Examples of the heat-resistant ribonucleases which can be preferably used include, but are not limited to, a commercially available ribonuclease, Hybridase™ Thermostable RNase H (Epicenter Technologies) as well as an RNase H from a thermophilic bacterium of the genus *Bacillus*, a bacterium of the genus *Thermus*, a bacterium of the genus *Pyrococcus*, a bacterium of the genus *Thermotoga*, a bacterium of the genus *Archaeoglobus* or the like. Furthermore, both of naturally occurring ribonucleases and variants can be preferably used. The enzymatic unit of RNase H indicated herein is a value expressed according to a method of measuring an enzymatic unit as described in Referential Examples.

The RNase H is not limited to a specific one as long as it can be used in the method of the present invention. For example, the RNase H may be derived from various viruses, phages, prokaryotes or eukaryotes. It may be either a cellular RNase H or a viral RNase H. The cellular RNase H is exemplified by *Escherichia coli* RNase HI and the viral RNase H is exemplified by HIV-1 RNase H. Type I, type II or type III RNase H can be used in the method of the present invention. For example, RNase HI from *Escherichia coli*, or RNase HII from a bacterium of the genus *Pyrococcus* or a bacterium of the genus *Archaeoglobus* is preferable, without limitation.

The efficiency of the cleavage reaction with an endonuclease such as RNase H used in the method of the present invention may vary depending on the nucleotide sequence around the 3' terminus of the primer and influence the amplification efficiency of the desired DNA. Therefore, it is natural to design the optimal primer for the RNase H used.

As used herein, the term "introducing a nick" or "nicking" means internally cleaving one of the two strands of a double-stranded nucleic acid. For example, an RNase H acts on a hybrid double-stranded nucleic acid composed of a DNA and a ribonucleotide-containing DNA to selectively cleave the ribonucleotide-containing strand among the two strands at the ribonucleotide portion, thereby introducing a nick into the hybrid double-stranded nucleic acid.

(4) DNA Polymerase Used in the Present Invention

A DNA polymerase having a strand displacement activity on a DNA can be used in the present invention. Particularly, a DNA polymerase substantially lacking a 5'→3' exonuclease activity can be preferably used.

Any DNA polymerases having the strand displacement activity can be used in the present invention. Examples thereof include variants of DNA polymerases lacking their 5'→3' exonuclease activities derived from thermophilic bacteria of the genus *Bacillus* such as *Bacillus caldotenax* (hereinafter referred to as *B. ca*) and *Bacillus stearothermophilus* (hereinafter referred to as *B. st*), as well as large fragment (Klenow fragment) of DNA polymerase I from *Escherichia coli* (*E. coli*). Both of mesophilic and heat-resistant DNA polymerases can be preferably used in the present invention.

*B. ca* is a thermophilic bacterium having an optimal growth temperature of about 70° C. Bca DNA polymerase from this bacterium is known to have a DNA-dependent DNA polymerase activity, an RNA-dependent DNA polymerase activity (a reverse transcription activity), a 5'→3' exonuclease activity and a 3'→5' exonuclease activity. The enzyme may be either an enzyme purified from its original source or a recombinant protein produced by using genetic engineering techniques. The enzyme may be subjected to modification such as substitution, deletion, addition or insertion by using genetic engineering techniques or other means. Examples of such enzymes include BcaBEST DNA polymerase (Takara Shuzo), which is *Bca*DNA polymerase lacking its 5'→3' exonuclease activity.

It is known that some DNA polymerases have an endonuclease activity such as an RNase H activity under specific conditions. Such a DNA polymerase can be used in the method of the present invention. In one aspect, the DNA polymerase may be used under conditions that allow the RNase H activity to express, e.g., in the presence of $Mn^{2+}$. In this case, the method of the present invention can be conducted without the addition of an RNase H. Thus, the Bca DNA polymerase can exhibit an RNase activity in a buffer containing $Mn^{2+}$. The above-mentioned aspect is not limited to the use of the *Bca* DNA polymerase. DNA polymerases that are known to have an RNase H activity such as Tth DNA polymerase from *Thermus thermophilus* can be used in the present invention.

(5) Method for Amplifying Target Nucleic Acid of the Present Invention

The method of the present invention can be conducted by using at least one chimeric oligonucleotide primer as described in (1) above, at least one upstream block oligonucleotide as described in (2) above, the endonuclease as described in (3) above and the DNA polymerase as described in (4) above in combination. Alternatively, a DNA polymerase having an RNase H activity can be used under conditions that allow the RNase H activity to express as described above.

dNTPs used for the PCR or the like (a mixture of dATP, dCTP, dGTP and dTTP) can be preferably used as nucleotide triphosphates that serve as substrates in the extension reaction in the method. In addition, dUTP may be used as a substrate. The dNTPs may contain a dNTP (deoxyribonucleotide triphosphate) analog such as 7-deaza-dGTP, triphosphate of dITP or the like as long as it serves as a substrate for the DNA polymerase used. A derivative of a dNTP or a dNTP analog may be used. A derivative having a functional group such as a dUTP having an amino group may be contained. A chimeric oligonucleotide primer is used in the method. The primer can be prepared, for example, using a DNA synthesizer according to a conventional synthesis method.

The amounts of the chimeric oligonucleotide primer and the upstream block oligonucleotide to be used in the method of the present invention may be adjusted depending on the nucleotide sequence of the target nucleic acid, the length of the fragment to be amplified and the composition of the reaction system to be used. For example, the amounts may be adjusted using the amount of amplification product as an index. In other words, there is no specific limitation concerning the amounts of the chimeric oligonucleotide primer and the block oligonucleotide to be used in the method of the present invention as long as an amplification product of interest is obtained.

According to the present invention, there is no specific limitation concerning the molar ratio of the chimeric oligonucleotide primer to the upstream block oligonucleotide to be used as long as the amplification product of interest is obtained.

In one embodiment of the method of the present invention, the molar ratio of the chimeric oligonucleotide primer to the upstream block oligonucleotide is, for example, 1:0.1 to 1:10, preferably 1:0.2 to 1:5, more preferably 1:0.25 to 1:4.

If the activity of the enzyme used may be decreased in the course of the reaction, the enzyme can be further added during the reaction in the method of the present invention. The added enzyme may be the same as that contained in the reaction mixture at the beginning of the reaction or it may be a different enzyme that exhibits the same activity. Thus, the type or the property of the enzyme to be added is not limited to a specific one as long as the addition during the reaction provides effects such as increase in the detection sensitivity or increase in the amount of amplification product.

The nucleic acid (DNA or RNA) used as a template in the method of the present invention may be prepared or isolated from any sample that may contain the nucleic acid. Alternatively, the sample may be used directly in the nucleic acid amplification reaction according to the present invention. Examples of the samples that may contain the nucleic acid include, but are not limited to, samples from organisms such as a whole blood, a serum, a buffy coat, a urine, feces, a cerebrospinal fluid, a seminal fluid, a saliva, a tissue (e.g., a cancerous tissue or a lymph node) and a cell culture (e.g., a mammalian cell culture or a bacterial cell culture), samples that contain a nucleic acid such as a viroid, a virus, a bacterium, a fungi, a yeast, a plant and an animal, samples suspected to be contaminated or infected with a microorganism such as a virus or a bacterium (e.g., a food or a biological formulation), and samples that may contain an organism such as a soil and a waste water. The sample may be a preparation containing a nucleic acid obtained by processing the above-mentioned samples according to a known method. Examples of the preparations that can be used in the present invention include a cell destruction product or a sample obtained by fractionating the product, the nucleic acid in the sample, or a sample in which specific nucleic acid molecules such as mRNAs are enriched. Furthermore, a nucleic acid such as a DNA or an RNA obtained amplifying a nucleic acid contained in the sample by a known method can be preferably used.

The preparation containing a nucleic acid can be prepared from the above-mentioned materials by using, for example, lysis with a detergent, sonication, shaking/stirring using glass beads or a French press, without limitation. In some cases, it is advantageous to further process the preparation to purify the nucleic acid (e.g., in case where an endogenous nuclease exists). In such cases, the nucleic acid is purified by a know method such as phenol extraction, chromatography, ion exchange, gel electrophoresis or density-gradient centrifugation.

When it is desired to amplify a nucleic acid having a sequence derived from an RNA, the method of the present invention may be conducted using as a template a cDNA synthesized by a reverse transcription reaction that uses the RNA as a template. Any RNA for which one can make a primer to be used in a reverse transcription reaction can be applied to the method of the present invention, including total RNA in a sample, RNA molecules such as, mRNA, tRNA and rRNA as well as specific RNA molecular species.

Any primer that anneals to an RNA as a template under reaction conditions used can be used in the reverse transcription reaction. The primer may be a primer having a nucleotide sequence that is complementary to a specific RNA as a template (a specific primer), an oligo-dT (deoxythymine) primer and a primer having a random sequence (a random primer). In view of specific annealing, the length of the primer for reverse transcription is preferably 6 nucleotides or more, more preferably 9 nucleotides or more. In view of oligonucleotide synthesis, the length is preferably 100 nucleotides or less, more preferably 30 nucleotides or less. A chimeric oligonucleotide primer can be used as a primer for reverse transcription. The chimeric oligonucleotide primer can be preferably utilized as a primer for a strand displacement reaction in the method for amplifying a nucleic acid of the present invention using a cDNA obtained after reverse transcription as a template. Such a primer may be any one that has the properties as described in (1) above and that can be used in a reverse transcription reaction from an RNA.

Any enzyme that has an activity of synthesizing a cDNA using an RNA as a template can be used in the reverse transcription reaction. Examples thereof include reverse transcriptases originating from various sources such as avian myeloblastosis virus-derived reverse transcriptase (AMV RTase), Molony murine leukemia virus-derived reverse transcriptase (MMLV RTase) and Rous-associated virus 2 reverse transcriptase (RAV-2 RTase). In addition, a DNA polymerase that also has a reverse transcription activity can be used. An enzyme having a reverse transcription activity at a high temperature such as a DNA polymerase from a bacterium of the genus *Thermus* (e.g., Tth DNA polymerase) and a DNA polymerase from a thermophilic bacterium of the genus *Bacillus* is preferable for the present invention. For example, DNA polymerases from thermophilic bacteria of the genus *Bacillus* such as a DNA polymerase from *B. st* (Bst DNA polymerase) and *Bca* DNA polymerase are preferable, although it is not intended to limit the present invention. For example, *Bca* DNA polymerase does not require a manganese ion for the reverse transcription reaction. Furthermore, it can synthesize a cDNA while suppressing the formation of a secondary structure of an RNA as a template under high-temperature conditions. Both a naturally occurring one and a variant of the enzyme having a reverse transcriptase activity can be used as long as they have the activity.

In another aspect, after duplicating a DNA or an RNA containing a nucleotide sequence to be amplified beforehand, the duplicated product may be used as a nucleic acid as a template in the method of the present invention. Examples of the methods for duplication include, but are not limited to, a method in which an appropriate host is transformed with a vector into which the nucleic acid fragment containing the nucleotide sequence to be amplified is inserted, the resulting transformant is cultured, the vector into which the nucleic acid fragment containing the nucleotide sequence to be amplified is inserted is extracted therefrom and used. Any vectors can be used as long as they are stably replicated in the host. For example, pUC series, pBluescript series, pGEM series, cosmid type. vectors and phage type vectors are preferably used. Any hosts can be used as long as they can maintain the vectors used. For example, the host is exemplified by *Escherichia coli*, which is readily cultured.

In another aspect of the duplication method, after an RNA having a nucleotide sequence to be amplified is transcribed using an RNA polymerase and a nucleic acid fragment containing the nucleotide sequence as a template, the RNA may be used as a template for the method of the present invention directly or after converting it into a cDNA by reverse transcription reaction. The nucleic acid fragment containing the nucleotide sequence to be amplified is not limited to a specific one as long as it has a promoter sequence for an RNA polymerase. It may be inserted into a vector having a promoter sequence for an RNA polymerase, ligated with an adapter or a cassette having a promoter sequence for an RNA polymerase at its end or enzymatically synthesized using a primer having a promoter sequence for an RNA polymerase and an appropriate template. Thus, a nucleic acid fragment containing a nucleotide sequence to be amplified can be duplicated or amplified in a form of an RNA using a promoter sequence for an RNA polymerase being positioned as described above. Any vectors can be used as long as they have promoter sequences for RNA polymerases. For example, pUC series, pBluescript series, pGEM series, cosmid type vectors and phage type vectors are preferably used. The vector can be preferably used in its circular form or after being linearized. Any RNA polymerases can be used for the duplication or amplification method. For example, SP6 RNA polymerase, T7 RNA polymerase, T3 RNA polymerase or the like can be preferably used.

Both of a double-stranded DNA such as a genomic DNA isolated as described above or a PCR fragment and a single-stranded DNA such as a cDNA prepared by a reverse transcription reaction from a total RNA or an mRNA can be preferably used as a template DNA in the present invention. The double-stranded DNA is preferably used after denaturing it into single-stranded DNAs or without such denaturation.

That is, the method of the present invention may or may not comprise a denaturation step.

In one embodiment of the present invention, if a nucleic acid having a sequence from an RNA is to be amplified, amplification reaction can be initiated by adding an RNA-cDNA double-stranded nucleic acid obtained by reverse transcription reaction using an RNA as a template to the amplification reaction mixture of the present invention containing an RNase H to digest the RNA strand and convert the nucleic acid into a single-stranded cDNA. Furthermore, a reverse transcription reaction using an RNA as a template and a DNA amplification reaction using a cDNA. generated by the reverse transcription reaction as a template can be conducted with one DNA polymerase in the DNA synthesis method of the present invention. Such a DNA polymerase has a reverse transcriptase activity and a strand displacement activity.

A nucleic acid is successively amplified under isothermal conditions after denaturing a double-stranded DNA into single-stranded DNAs or, if an RNA is used as a template, preparing a cDNA (a single-stranded DNA) by a reverse transcription reaction.

"Successively" means that a reaction proceeds without a change in the reaction temperature or the composition of the reaction mixture. As used herein, "isothermal" means conditions of a substantially constant temperature under which an enzyme and a nucleic acid strand function in each step.

The nucleic acid amplification reaction of the present invention may be conducted at a normal temperature (e.g., 37° C.) by using a mesophilic DNA polymerase such as Klenow fragment. It can also be conducted at a high temperature (e.g., 50° C. or higher) by using heat-resistant enzymes (an endonuclease and a DNA polymerase). In this case, non-specific annealing of a primer is suppressed, resulting in increase in the specificity of DNA amplification. Furthermore, the problem of forming secondary structure of a DNA as a template is solved, resulting in increase in the ability of extension of a DNA polymerase. A reverse transcription reaction and the nucleic acid amplification can be successively conducted in the method. In this case, a DNA having a sequence derived from an RNA can be amplified by combining the use of a reverse transcriptase with the above-mentioned reaction or by using a DNA polymerase having a reverse transcription activity.

In each aspect of the present invention, preferably, a chimeric oligonucleotide primer and an upstream block oligonucleotide that are complementary to a DNA as a template are annealed to the DNA, although it is not intended to limit the present invention. A DNA that is complementary to the DNA as the template (a primer-extended strand) is then extended along the remained sequence of the DNA as the template from the 3' terminus of the chimeric oligonucleotide primer by the action of a DNA polymerase having a strand displacement activity. Then, the strand extended from the chimeric oligonucleotide primer is blocked by annealing of the upstream block oligonucleotide, which is substantially complementary to a nucleotide sequence 3' to the region in the nucleic acid as the template substantially complementary to the chimeric oligonucleotide primer, to the nucleic acid as the template. As a result, a template for non-linear amplification to which the chimeric oligonucleotide primer anneals is amplified in the early reaction stage in the method of the present invention. The early amplification reaction stably increases the amplification efficiency of the method of the present invention. Consequently, the sensitivity of detecting a target nucleic acid is increased.

In one aspect of the present invention, the endonuclease acts as a nicking enzyme that introduces a nick into the double-stranded DNA or it alters the structure of the double-stranded DNA composed of the chimeric oligonucleotide primer and the DNA as the template, although the present invention is not restricted by a theory. A DNA polymerase having a strand displacement activity re-extends a DNA strand from the 3' terminus of the nick introduced in the double-stranded DNA to generate a new primer-extended strand while releasing the DNA downstream from the 3' terminus of the nick. Thus, the new primer-extended strand replaces the previously synthesized primer-extended strand.

The method for amplifying a nucleic acid of the present invention can be carried out using a pair of primers and a pair of block oligonucleotides, i.e., a chimeric oligonucleotide primer and an upstream block oligonucleotide that are complementary to a nucleic acid as a template and another chimeric oligonucleotide primer and another upstream block oligonucleotide that are complementary to a displaced strand. In this case, it is considered that chimeric oligonucleotide primers bind to a double-stranded DNA to synthesize respective complementary strands, and upstream block oligonucleotides anneal to the respective complementary strands, thereby blocking annealing of the respective complementary strands to each other at the portions to which the upstream block oligonucleotides anneal. In addition, it is considered that a template switching reaction also proceed in parallel in the extension reaction. It is clear that a reaction product with one primer can function as a template for another primer if this aspect is used. Thus, the amount of amplification product increases in a non-linear manner as the amount of the template increases.

When the method for amplifying a nucleic acid of the present invention is conducted using a double-stranded DNA as a template, both strands can serve as templates in the amplification reaction by using chimeric oligonucleotide primers and upstream block oligonucleotides that anneal to the respective two strands. If the reaction is initiated using a double-stranded DNA as a template, a chimeric oligonucleotide primer, an upstream block oligonucleotide, four deoxyribonucleotide triphosphates (dNTPs), a DNA polymerase and an endonuclease are added to a reaction mixture. If heat treatment is used for denaturing the double-stranded DNA and a heat-resistant enzyme is not used, it is preferable to add the enzyme after the denaturation.

In the aspect of the nucleic acid amplification method of the present invention in which a double-stranded DNA as a template, two chimeric oligonucleotide primers and two upstream block oligonucleotides are used, switching of templates may occur among the template-extended strand intermediates during the extension reaction from the primers to generate a double-stranded nucleic acid consisting of the synthesized primer-extended strands being annealed each other, although it depends on the reaction conditions or the like. The double-stranded nucleic acid has chimeric oligonucleotide primers at both ends. Then, reactions of extending complementary strands comprising strand displacement can be initiated from both of the ends again. As a result of the reaction, an amplification product having the primer sequence at one end is generated. Furthermore, if switching of templates occurs during the reaction, a double-stranded nucleic acid similar to one that described above is generated again.

The present invention provides a method for amplifying a nucleic acid which comprises using a DNA polymerase having a strand displacement activity to effect a template switching reaction. In the template switching reaction in the presence of a double-stranded nucleic acid as a template, two chimeric oligonucleotide primers and two upstream block oligonucleotides that are substantially complementary to the nucleotide sequences of the respective strands as well as a DNA polymerase having a strand displacement activity, two primer-extended strands complementary to the template are synthesized. Template switching of each of the primer-extended strands from the template to the other primer-extended strand takes place during the synthesis of the primer-extended strands.

As used herein, a template switching reaction refers to a reaction in which, when complementary strands are synthesized by strand displacement reactions from the both sides of a double-stranded nucleic acid, a DNA polymerase switches the template and synthesizes a complementary strand thereafter using the other complementary strand newly synthesized by another DNA polymerase as a template. In other words, a template switching reaction refers to a reaction in which a double-stranded nucleic acid as a template is treated with primers and a DNA polymerase having a strand displacement activity to generate extended strands complementary to the template, wherein a DNA polymerase that synthesized the primer-extended strands actively switches the template from the original templates to the other primer-extended strands during the synthesis of the extended strands.

A DNA polymerase capable of effecting the template switching reaction during strand displacement reaction can be preferably used for the present invention. For example, a variant enzyme of Bca DNA polymerase lacking a 5' 3' exonuclease activity is preferably used in particular. Such an enzyme is commercially available as BcaBEST DNA polymerase (Takara Shuzo). It can also be prepared from Escherichia coli HB101/pUI205 (FERM BP-3720) which contains the gene for the enzyme according to the method as described in Japanese Patent No. 2978001.

In the amplification method of the present invention, the chimeric oligonucleotide primer-extended strand may be cleaved at a site that contains the ribonucleotide such that the 5' fragment (primer portion) resulting from the cleavage does not contain the ribonucleotide. A primer-extended strand extended from the thus generated primer portion is no longer cleaved by an endonuclease. As a result, an amplification product having the primer sequence at its end is generated.

As described above, an amplification product without the primer sequence and a product having the primer sequence(s) at one or both of the ends may be generated in the nucleic acid amplification method of the present invention. These products are included in the amplification products herein.

In the nucleic acid amplification method of the present invention using a chimeric oligonucleotide primer, a polymer in which the regions to be amplified are connected each other may be generated. The polymer has a structure in which plural regions to be amplified are repeated in the same direction. The polymers are observed upon electrophoretic analyses of amplification products as laddered bands. It is considered that the generation of such polymers is influenced by the region to be amplified, the size of the region, the flanking regions, the nucleotide sequence of the chimeric oligonucleotide primer to be used, the reaction conditions and the like.

The polymer as described above contains plural regions to be amplified. For example, the polymer is useful when detection of a nucleic acid containing a region to be amplified is intended because it hybridizes to a number of probes upon hybridization using an appropriate probe and generates a intensive signal. The region to be amplified or a portion thereof can be obtained from the polymer as a monomer by using digestion with a restriction enzyme or the like in combination.

The DNA polymerase used in the present invention should synthesize an extended strand from the 3' terminus of the primer portion towards the downstream while displacing a previously extended DNA strand. It is important that the DNA polymerase should not exhibit a 5'→3' exonuclease activity that may digest the displaced strand. For example, Klenow fragment, which is an exonuclease-deficient variant of DNA polymerase I from *Escherichia coli*, a similar fragment derived from *Bst* DNA polymerase (New England Biolabs), and BcaBEST DNA polymerase from *B. ca* (Takara Shuzo) are useful as such a DNA polymerase. Sequenase 1.0 and Sequenase 2.0 (United States Biochemical), and T5 DNA polymerase and φ29 DNA polymerase as described in Gene, 97:13–19 (1991) can also be used. A polymerase that normally has a 5'→3' exonuclease activity can be used in the DNA synthesis method of the present invention if addition of an appropriate inhibitor can inhibit the activity.

The method for amplifying a nucleic acid of the present invention may be conducted at varying temperatures or it may be conducted isothermally. Varying temperatures mean that the reaction temperatures are changed for respective steps such that the change does not interfere with the reactions in the steps. Specifically, varying temperatures refer to change in temperature to that suitable for, for example, each of annealing of a primer, a reaction of complementary strand synthesis, nicking of a complementary strand and a displacement reaction.

On the other hand, isothermal means that the reaction temperature for each step is unchanged and each step is conducted at a substantially constant temperature. It is natural to select the temperature to optimize the reaction conditions in both cases.

One feature of the method for amplifying a nucleic acid of the present invention is that the method does not require adjusting the temperature up and down during the nucleic acid synthesis. Thus, the present invention provides a method for isothermally synthesizing a nucleic acid. Many of conventional nucleic acid amplification methods require adjusting the temperature up and down to dissociate a target from a synthesized strand. These methods require special reaction equipment such as a thermal cycler for this purpose. However, the method of the present invention can be conducted only using equipment that can keep a constant temperature. As described above, the method of the present invention can be conducted at a single temperature. Preferably, it is conducted by selecting the reaction temperature and the stringency level such that non-specific annealing of a primer is reduced and such that the primer specifically anneals to a nucleic acid as a template. Although it is not intended to limit the present invention, the method of the present invention can be conducted under high-temperature conditions by using a heat-resistant enzyme as described above. In addition, it is preferable to conduct the method of the present invention at an appropriate temperature for sufficiently retaining the activity of the enzyme used in order to maintain the reaction efficiency at high level. Thus, the reaction temperature is preferably about 20° C. to about 80° C., more preferably about 30° C. to about 75° C., most preferably about 50° C. to about 70° C. although it varies depending on the enzyme used. When the reaction is conducted under high-temperature conditions in particular, it is preferable to use a longer primer than that for a reaction at a normal temperature. For example, when a reaction temperature of 55° C. to 60° C. or 65° C. is used, the primer or block oligonucleotide used for the method of the present invention may be, for example, without limitation, about 6 to about 100 nucleotides in length, preferably about 10 to about 50 nucleotides in length, more preferably about 12 to about 40 nucleotides in length. An example of effects brought by the elevated reaction temperature is the solution of a problem of forming secondary structure of a DNA as a template. The elevated reaction temperature enables amplification of a desired nucleic acid even if a nucleic acid having a high GC content is used as a template. Furthermore, it is similarly effective in amplifying a region of a long chain length. Such effect is observed in a range between about 60 bp and about 20 kbp, specifically between about 60 bp and about 4.3 kbp, more specifically about 60 bp and about 1500 bp.

Use of a DNA polymerase having a reverse transcriptase activity (e.g., BcaBEST DNA polymerase) in the method of the present invention can make the amplification of a nucleic acid from an RNA, which comprises a step of preparing a cDNA from an RNA (a reverse transcription reaction), be conveniently conducted using only a single enzyme. Alternatively, a product obtained by independently conducting a step of preparing a cDNA from an RNA, i.e., a cDNA, can be used in the method of the present invention as the DNA as a template.

In each case, the reaction in the method of the present invention is repeated until it is terminated by appropriate means, for example, by inactivating the enzyme or by lowering the reaction temperature, or until the reaction is deprived of one of the substrates.

The method for amplifying a nucleic acid of the present invention can be used for various experimental procedures that utilize amplification of a nucleic acid including detection, labeling and sequencing of a nucleic acid.

Furthermore, the method for amplifying a nucleic acid of the present invention can be used for an in situ nucleic acid amplification method, a method for amplifying a nucleic acid on a solid substrate such as a DNA chip, or a multiplex nucleic acid amplification method in which plural regions are simultaneously amplified.

The upstream block oligonucleotide according to the present invention can be used in a so-called asymmetric nucleic acid amplification method in which an amplification reaction is carried out using an excess amount of one primer relative to another.

According to the method for amplifying a nucleic acid of the present invention, a single-stranded DNA substantially free of a complementary strand thereto can be prepared. For example, a single-stranded DNA for producing a material having an immobilized nucleic acid such as a DNA chip, a single-stranded DNA probe for detecting a target nucleic acid, or a mega-primer for the long-chain PCR can be readily produced in a short time. Only a sense sequence or an antisense sequence can be selectively amplified by using the method of the present invention. Thus, the present invention is also useful as a method for producing a nucleic acid having a sense sequence or a antisense sequence.

A region of a nucleic acid of interest can be amplified even from a trace amount of a nucleic acid as a template by conducting the method of the present invention in a buffer of Bicine, Tricine, HEPES, phosphate or tris.

Furthermore, the methods for amplifying a nucleic acid of the present invention does not require the reaction equipment that can adjust a temperature with the passage of time. Therefore, an amplification reaction can be conducted in a large volume of reaction mixture. Thus, a nucleic acid (e.g., for medical use) can be industrially produced in large quantities.

The nucleic acid amplification method of the present invention can produce an amplification product with high fidelity to the nucleotide sequence of the template nucleic acid. When the frequency of error in the DNA synthesis in the method of the present invention was confirmed by analyzing the nucleotide sequences of resulting amplification products, the frequency of error found in amplification products obtained by the method of the present invention was equivalent to that by LA-PCR which is known to be able to amplify a nucleic acid with high fidelity. In other words, the method of the present invention has fidelity equivalent to that of the LA-PCR.

(6) Kit of the Present Invention

The present invention provides a kit used for the method for amplifying a nucleic acid of present invention as described above. In one embodiment, the kit is in a packed form and contains instructions regarding the use of a DNA polymerase, an endonuclease, a chimeric oligonucleotide primer and an upstream block oligonucleotide in a strand displacement reaction. Also, a kit that contains a DNA polymerase having a strand displacement activity, an endonuclease, and a buffer for a strand displacement reaction is preferably used for the method of the present invention. Alternatively, a commercially available DNA polymerase having a strand displacement activity and/or endonuclease may be selected and used according to the instructions. Additionally, the kit may contain a reagent for a reverse transcription reaction that is used when an RNA is used as a template. The DNA polymerase can be selected from the DNA polymerases to be used in the present invention as described in (4) above. The endonuclease can be selected from the endonucleases as described in (3) above.

"Instructions" are printed matters describing a method of using the kit, e.g., a method for preparing a reagent solution for a strand displacement reaction, recommended reaction conditions and the like. The instructions include an instruction manual in a form of a pamphlet or a leaflet, a label stuck to the kit, and description on the surface of the package containing the kit. The instructions also include information disclosed or provided through electronic media such as the Internet.

The kit of the present invention may further contain a reaction buffer containing Bicine, Tricine, HEPES, phosphate or tris as a buffering component and an annealing solution. Additionally, it may contain a DNA polymerase having a strand displacement activity and an RNase H. Furthermore, the kit may contain a modified deoxyribonucleotide or a deoxynucleotide triphosphate analog.

The kit used in the method for detecting a target nucleic acid may further contain an appropriate chimeric oligonucleotide primer and an appropriate upstream block oligonucleotide for amplifying the target nucleic acid and a reagent for detecting the amplified target nucleic acid such as a probe in addition to the instructions and the reagents for amplification reaction as described above.

In addition, the kits of the present invention include a kit containing the chimeric oligonucleotide primer and the upstream block oligonucleotide used in the present invention and/or the probe of the present invention as described above.

(7) Composition of the Present Invention

The present invention provides a composition used for the method for amplifying a nucleic acid of the present invention or the method for detecting a nucleic acid of the present invention as described above. For example, the composition may contain the chimeric oligonucleotide primer as described in (1) above, the upstream block oligonucleotide as described in (2) above, the endonuclease as described in (3) above and the DNA polymerase as described in (4) above. The composition may further contain a buffering component, a magnesium salt, dNTPs and the like as components for conducting an amplification reaction. Furthermore, it may contain a modified deoxyribonucleotide or a deoxynucleotide triphosphate analog. Additionally, buffering component and other additives can be used.

In a particularly preferable aspect, the composition may contain suitable amounts of the various components as listed above for the nucleic acid amplification method of the present invention. Amplification reaction can be conducted only by adding an appropriate template, chimeric oligonucleotide primer(s) and upstream block oligonucleotide(s) to the composition. If the object to be amplified is known beforehand, the composition preferably contains chimeric oligonucleotide primer(s) suitable for amplifying the object.

(8) Method for Detecting Target Nucleic Acid of the Present Invention

A target nucleic acid in a sample can be detected by using the method for amplifying a nucleic acid of the present invention. The detection method comprises:

(a) amplifying a target nucleic acid by the method for amplifying a nucleic acid of the present invention as described above; and (b) detecting the target nucleic acid amplified in the step above.

In step (a) above, if an RNA is used as a template, the reverse transcription reaction and the nucleic acid amplification reaction may be conducted in one step. Although it is not intended to limit the present invention, for example, a combination of AMV RTase, MMLV RTase or RAV-2 RTase and Bca DNA polymerase can be preferably used as a combination of a reverse transcriptase and a strand displacement-type DNA polymerase.

The method can be utilized to detect or quantify a specific gene in a sample. In other words, a specific gene can be detected or quantified from all samples suspected to contain a nucleic acid such as a DNA or an RNA. Examples of the samples from which a specific gene can be detected or quantified include, but are not limited to, samples from organisms such as whole blood, serum, buffy coat, urine, feces, cerebrospinal fluid, seminal fluid, saliva, tissue (e.g., a cancerous tissue or a lymph node) and a cell culture (e.g., a mammalian cell culture or a bacterial cell culture), samples that contain a nucleic acid such as a viroid, a virus, a bacterium, a fungus, a yeast, a plant and an animal, samples suspected to be contaminated or infected with a microorganism such as a virus or a bacterium (e.g., a food or a biological formulation), and samples that may contain an organism such as a soil and a waste water. For example, a viroid, a virus, a fungus, a bacterium or other microorganisms in a sample can be detected or quantified on the basis of the presence or the content of a specific gene derived from these microorganisms as a target. Particularly, a method for detecting a pathogenic microorganism is useful in fields of sanitation and environment. Furthermore, the method of the present invention can be used to distinguish a genotype of an organism or to determine the expression level of a gene. Particularly, detection or confirmation of the expression state of a disease-related gene, e.g., a gene related to canceration of cells is useful in a field of medicine. Both of an RNA and a DNA can be preferably used as the nucleic acid as the template in the detection.

Furthermore, the method for detecting a target nucleic acid of the present invention can be used as a method for typing of a genetic polymorphism of a target nucleic acid.

Although it is not intended to limit the present invention, for example, the chimeric oligonucleotide primer to be used is designed such that the 3'-terminal portion of the primer is positioned close to the specific base of the target nucleotide sequence to be distinguished. For example, it is designed such that a hydrogen bond is formed between the base and the 3'-terminal base of the primer. If a mismatch exists between the nucleotide sequence of the 3'-terminal portion of the primer and the nucleotide sequence of the template, amplification from the target nucleic acid does not take place and no amplification product is generated using the above-mentioned chimeric oligonucleotide primer for amplification reaction. Information concerning a specific base in a gene such as a point mutation or a single nucleotide polymorphism (SNP) can be obtained using the method.

Similarly, the method of the present invention can be used as a method for typing of a genetic polymorphism such as a deletion mutation or an insertion mutation.

The upstream block oligonucleotide according to the present invention can be used in the method for typing of genetic polymorphisms as described in PCT/JP02/01222.

In one embodiment, the upstream block oligonucleotide according to the present invention may be used in combination with a Nucleotide in a method for typing of genetic polymorphisms in a target nucleic acid, the method comprising:

(1) mixing a sample containing a target nucleic acid with a Nucleotide, wherein the Nucleotide (A) is modified at the 3' terminus such that extension from the terminus by a DNA polymerase does not occur;

(B) has a base sequence capable of annealing to a region containing a specific base in the target nucleic acid; and (C) contains a sequence in which if there is a mismatch between the specific base and a base corresponding to the specific base in the Nucleotide in a complex composed of the Nucleotide and the target nucleic acid, the Nucleotide is not cleaved with a nuclease, and if there is no mismatch between the specific base and a base corresponding to the specific base in the Nucleotide, the Nucleotide is cleaved with a nuclease to generate a new 3' terminus;

(2) treating the mixture with the nuclease and the DNA polymerase; and (3) detecting the presence of cleavage of the Nucleotide with the nuclease.

In another embodiment, the upstream block oligonucleotide according to the present invention may be used in combination in a method for typing of genetic polymorphisms in a target nucleic acid, the method comprising:

(1) mixing a sample containing a target nucleic acid with a Nucleotide, wherein the Nucleotide (A) is modified at the 3' terminus such that extension from the terminus by a DNA polymerase does not occur;

(B) has a base sequence capable of annealing to a region containing a specific base in the target nucleic acid; and (C) contains a sequence in which if there is no mismatch between the specific base and a base corresponding to the specific base in the Nucleotide in a complex composed of the Nucleotide and the target nucleic acid, the Nucleotide is not cleaved with a nuclease, and if there is a mismatch between the specific base and a base corresponding to the specific base in the Nucleotide, the Nucleotide is cleaved with a nuclease to generate a new 3' terminus;

(2) treating the mixture with the nuclease and the DNA polymerase; and (3) detecting the presence of cleavage of the Nucleotide with the nuclease.

As used herein, "a genetic polymorphism" refers to a difference in a nucleotide sequence of a gene among individuals in the same organism population. Differences in nucleotide sequences constituting "genetic polymorphisms" are not limited to specific forms, but include various types such as "base substitutions", "deletion mutations" and "insertion mutations." The difference in genetic information is also called a variation.

"A base substitution" refers to replacement of a nucleotide at a specific site in a nucleic acid by another nucleotide. "Base substitutions" include "single nucleotide polymorphisms (SNP)."

"A deletion mutation" refers to partial or entire deletion of a nucleotide sequence at a specific site in a nucleic acid.

"An insertion mutation" refers to insertion of a nucleotide sequence of an arbitrary chain length at a specific site in a nucleic acid.

In the above-mentioned embodiment, the block oligonucleotide according to the present invention anneals to a portion upstream of the Nucleotide in a target nucleic acid. As a result, detection sensitivity in typing of genetic polymorphisms in a target nucleic acid can be increased like the method for amplifying a target nucleic acid of the present invention.

The method for detecting a target nucleic acid of the present invention can be conducted by amplifying the target nucleic acid directly from a sample containing the nucleic acid. In this case, the chain length of the target nucleic acid to be amplified is not limited to a specific one. For example, a region of 200 bp or shorter, preferably 150 bp or shorter is effective for sensitive detection of the target nucleic acid. The target nucleic acid in the sample can be detected with high sensitivity by designing the chimeric oligonucleotide primers of the present invention to result in the chain length to be amplified as described above.

In addition, a target nucleic acid can be detected with more sensitivity even from a trace amount of a nucleic acid sample in the detection method of the present invention by using a reaction buffer containing Bicine, Tricine, HEPES, phosphate or tris as a buffering component and an annealing solution containing spermidine or propylenediamine. In this case, the endonuclease and the DNA polymerase to be used are not limited to specific ones. For example, a combination of Afu RNase H and BcaBEST DNA polymerase is preferable. It is considered that the preferable units of the endonuclease and the DNA polymerase may vary depending on the types the enzymes. In such a case, the composition of the buffer and the amounts of the enzymes added may be adjusted using the increase in detection sensitivity or the amount of amplification product as an index.

In the detection method of the present invention, dUTP may be incorporated as a substrate during amplification of a target nucleic acid. Thus, if dUTP is used as a substrate, it is possible to prevent false positives due to carry-over contamination of amplification products by degrading amplification products utilizing uracil N-glycosidase (UNG).

Known methods for detecting a nucleic acid can be used for step (b) Examples of such methods include detection of a reaction product having a specific size by electrophoresis, and detection by hybridization with a probe. Furthermore, a detection method in which magnetic beads are used in combination can be preferably used. A fluorescent substance such as ethidium bromide is usually used in the detection by electrophoresis. The hybridization with a probe may be combined with the detection by electrophoresis. The probe may be labeled with a radioisotope or with a non-radioactive substance such as biotin or a fluorescent substance. Additionally, use of a labeled nucleotide in step (a) may facilitate the detection of amplification product into which the labeled nucleotide is incorporated, or may enhance the signal for detection utilizing the label. A fluorescence polarization method, a fluorescence energy transition or the like can also be utilized for the detection. The target nucleic acid can be detected automatically or quantified by constructing a suitable detection system. In addition, detection with naked eyes by a hybrid chromatography method can be preferably used.

A ribonucleotide (RNA) probe, or a chimeric oligonucleotide probe composed of a ribonucleotide and a deoxyribonucleotide, labeled with two or more fluorescent substances positioned at a distance that results in a quenching state can be used in the detection method of the present invention. The probe does not emit fluorescence. When it is annealed to a DNA amplified from a target nucleic acid that is complementary to the probe, RNase H digests the probe. The distance between the fluorescent substances on the probe then increases, resulting in the emission of fluorescence. Thus, the emission reveals the presence of the target nucleic acid. If RNase H is used in the method for amplifying a nucleic acid of the present invention, a target nucleic acid can be detected only by adding the probe to the reaction mixture. For example, a combination of fluorescent substances, 6-carboxyfluorescein (6-FAM) and N,N,N',N'-tetramethyl-6-carboxyrhodamine (TAMRA), can be preferably used for labeling the probe.

The present invention further provides a probe used in the above-mentioned method for detecting a target nucleic acid. The probe of the present invention is not limited to specific one as long as it can hybridize to a target nucleic acid amplified by the nucleic acid amplification method of the present invention under normal hybridization conditions. In view of specific detection of amplification product, a probe that hybridizes under conditions, for example, known to those skilled in the art as being stringent is preferable. The stringent hybridization conditions are described in, for example, T. Maniatis et al. (eds.), Molecular Cloning: A Laboratory Manual 2nd ed., 1989, Cold Spring Harbor Laboratory. Specifically, the stringent conditions are exemplified by the following: incubation at a temperature about 25° C. lower than the Tm of the probe to be used for 4 hours to overnight in 6×SSC (1×SSC: 0.15 M NaCl, 0.015 M sodium citrate, pH 7.0) containing 0.5% SDS, 5×Denhardt's (0.1% bovine serum albumin (BSA), 0.1% polyvinylpyrrolidone, 0.1% Ficoll 400) and 100 μg/ml salmon sperm DNA. A probe having a label as described above may be used as the probe for facilitating the detection of the target nucleic acid.

The method of the present invention does not require the use of equipment such as a thermal cycler. The sensitivity of detecting a target nucleic acid can be increased according to the method of the present invention by using a chimeric oligonucleotide primer and an upstream block oligonucleotide in combination. Reagents such as dNTPs used for PCR and the like can be applied to the method of the present invention. Therefore, the method of the present invention can be preferably used, for example, in a field of genetic test in which the detection is routinely conducted. The method of the present invention provides a greater amount of an amplification product in a shorter time than the PCR. Therefore, the method of the present invention can be utilized as a convenient, rapid and sensitive method for detecting a gene.

In genetic analysis on a genomic level, attempts are made to make the reaction system small and to increase the degree of integration in order to analyze a large amount of nucleotide sequences. A system has been developed for this purpose by utilizing the latest hyperfine processing techniques in which basic processes for genome analysis (e.g., extraction of DNA from cells, DNA amplification reaction, electrophoresis, hybridization, detection of the DNA of interest, etc.) are integrated on a microchip of several square centimeters to fingertip size. Such a system is referred to as a microchip or a nanochip.

Application of the PCR to the system as a gene amplification reaction is currently considered. However, since the PCR requires means for repeatedly controlling temperature up and down over time, the system would become complicated. By contrast, since the system can be simplified using the method of the present invention which can amplify a nucleic acid under isothermal conditions, the method is quite suitably utilized for the integrated system as described above. A highly integrated system can be constructed by utilizing the techniques of the present invention.

EXAMPLES

The following examples further illustrate the present invention in detail but are not to be construed to limit the scope thereof.

Referential Example 1

Cloning of RNase HII Gene from *Archaeoglobus fulgidus*

(1) Preparation of Genomic DNA from *Archaeoglobus fulgidus*

Cells of *Archaeoglobus fulgidus* (purchased from Deutsche Sammlung von Mikroorganismen und Zellkulturen GmbH; DSM4139) collected from 8 ml of a culture was suspended in 100 μl of 25% sucrose, 50 mM tris-HCl (pH 8.0). 20 μl of 0.5 M EDTA and 10 μl of 10 mg/ml lysozyme chloride (Nacalai Tesque) in water was added thereto. The mixture was reacted at 20° C. for 1 hour. After reaction, 800 μl of a mixture containing 150 mM NaCl, 1 mM EDTA and 20 mM tris-HCl (pH 8.0), 10 μl of 20 mg/ml proteinase K (Takara Shuzo) and 50 μl of 10% aqueous solution of sodium lauryl sulfate were added to the reaction mixture. The mixture was incubated at 37° C. for 1 hour. After reaction, the mixture was subjected to phenol-chloroform extraction, ethanol precipitation and air-drying, and then dissolved in 50 μl of TE to obtain a genomic DNA solution.

(2) Cloning of RNase HII Gene

The entire genomic sequence of the *Archaeoglobus fulgidus* has been published [Nature, 390:364–370 (1997)]. The existence of one gene encoding a homologue of RNase HII (AF0621) was known (SEQ ID NO:1, http://www.tigr.org/tdb/CMR/btm/htmls/SplashPage.htlm).

Primers AfuNde (SEQ ID NO:2) and AfuBam (SEQ ID NO:3) were synthesized on the basis of the sequence of the AF0621 gene (SEQ ID NO:1).

A PCR was carried out using 30 ng of the *Archaeoglobus fulgidus* genomic DNA prepared in (1) as a template, and 20 pmol each of AfuNde and AfuBam as primers in a volume of 100 μl. Pyrobest DNA polymerase (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.6 kb was digested with NdeI and BamHI (both from Takara Shuzo). Then, a plasmid pAFU204 was constructed by incorporating the resulting DNA fragment between NdeI and BamHI sites in a plasmid vector pTV119Nd (a plasmid in which the NcoI site in pTV119N is converted into a NdeI site).

(3) Determination of Nucleotide Sequence of DNA Fragment Containing RNase HII Gene The nucleotide sequence of the DNA fragment inserted into pAFU204 obtained in (2) was determined according to a dideoxy method.

Analysis of the determined nucleotide sequence revealed an open reading frame presumably encoding RNase HII. The nucleotide sequence of the open reading frame is shown in SEQ ID NO:4. The amino acid sequence of RNase HII deduced from the nucleotide sequence is shown in SEQ ID NO:5.

*Escherichia coli* JM109 transformed with the plasmid pAFU204 is designated and indicated as *Escherichia coli* JM109/pAFU204, and deposited on Feb. 22, 2001 at International Patent Organism Depositary, National Institute of Advanced Industrial Science and Technology, AIST Tsukuba. Central 6, 1-1, Higashi 1-chome, Tsukuba-shi, Ibaraki 305-8566, Japan under accession number FERM P-18221, and deposited at International Patent Organism Depositary, National Institute of Advanced Industrial Science and Technology under accession number FERM BP-7691 (date of request for transmission to international depositary authority: Aug. 2, 2001).

(4) Preparation of Purified RNase HII Preparation

*Escherichia coli* JM109 was transformed with pAFU204 obtained in (2). The resulting *Escherichia coli* JM109 harboring pAFU204 was inoculated into 2 L of LB medium containing 100 µg/ml of ampicillin and cultured with shaking at 37° C. for 16 hours. After cultivation, cells collected by centrifugation were suspended in 37.1 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12000 rpm for 10 minutes was heated at 70° C. for 15 minutes. It was then centrifuged at 12000 rpm for 10 minutes again to collect a supernatant. Thus, 40.3 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

The flow-through RNase HII fraction was subjected to RESOURSE S column (Amersham Pharmacia Biotech) equilibrated with Buffer A and chromatographed using FPLC system (Amersham Pharmacia Biotech). As a result, RNase HII flowed through the RESOURSE S column.

40.0 ml of the flow-through RNase HII fraction was dialyzed against 2 L of Buffer B (50 mM tris-HCl (pH 7.0), 1 mM EDTA) containing 50 mM NaCl for 2 hours. The dialysis was repeated two more times. 40.2 ml of the dialyzed enzyme solution was subjected to HiTrap-heparin column (Amersham Pharmacia Biotech) equilibrated with Buffer B containing 50 mM NaCl and eluted with a linear gradient of 50 to 550 mM NaCl using FPLC system. As a result, a fraction containing RNase HII eluted with about 240 mM NaCl was obtained.

7.8 ml of the RNase HII fraction was concentrated by ultrafiltration using Centricon-10 (Amicon). Four portions each separated from about 600 µl of the concentrate were subjected to Superose 6 gel filtration column (Amersham Pharmacia Biotech) equilibrated with 50 mM tris-HCl (pH 7.0) containing 100 mM NaCl and 0.1 mM EDTA and eluted with the same buffer. As a result, RNase HII was eluted at a position corresponding to a molecular weight of 30.0 kilodalton. This molecular weight corresponds to that of the RNase HII in the monomeric form.

The RNase HII eluted as described above was used as Afu RNase HII preparation.

The enzymatic activity of the thus obtained Afu RNase HII preparation was measured as follows.

100 µl of a reaction mixture [20 mM HEPES-potassium hydroxide (pH 7.8), 0.01% bovine serum albumin (Takara Shuzo), 1% dimethyl sulfoxide, 4 mM manganese acetate, 20 µg/ml poly(dT) (Amersham Pharmacia Biotech), 30 µg/ml poly(rA) (Amersham Pharmacia Biotech)] which had been incubated at 40° C. was added to 1 µl of the Afu RNase HII preparation. The mixture was reacted at 40° C. for 10 minutes. The reaction was then terminated by adding 10 µl of 0.5 M EDTA (pH 8.0). Absorbance at 260 nm was then measured. As a result, an RNase H activity was observed for the Afu RNase HII preparation.

Unit number of a heat-resistant RNase H was calculated as follows.

1 mg of poly(rA) or poly(dT) (both from Amersham Pharmacia Biotech) was dissolved in 1 ml of 40 mM tris-HCl (pH 7.7) containing 1 mM EDTA to prepare a poly(rA) solution and a poly(dT) solution.

The poly(rA) solution (to a final concentration of 20 µg/ml) and the poly(dT) solution (to a final concentration of 30 µg/ml) were then added to 40 mM tris-HCl (pH 7.7) containing 4 mM $MgCl_2$, 1 mM DTT, 0.003% BSA and 4% glycerol. The mixture was reacted at 37° C. for 10 minutes and then cooled to 4° C. at prepare a poly(rA)-poly(dT) solution. 1 µl of an appropriate dilution of an enzyme solution was added to 100 µl of the poly(rA)-poly(dT) solution. The mixture was reacted at 40° C. for 10 minutes. 10 µl of 0.5 M EDTA was added thereto to terminate the reaction. Absorbance at 260 nm was then measured. As a control, 10 µl of 0.5 M EDTA was added to the reaction mixture, the resulting mixture was reacted at 40° C. for 10 minutes, and the absorbance was then measured. A value (difference in absorbance) was obtained by subtracting the absorbance for the control from the absorbance for the reaction in the absence of EDTA. Thus, the concentration of nucleotide released from poly(rA)-poly(dT) hybrid by the enzymatic reaction was determined on the basis of the difference in absorbance. One unit of an RNase H was defined as an amount of enzyme that increases $A_{260}$ corresponding to release of 1 nmol of ribonucleotide in 10 minutes calculated according to the following equation:

Unit=[Difference in Absorbance×Reaction Volume (ml)]/0.0152×(110/100)×Dilution Rate Example 1

(1) Design of Primers and Block Oligonucleotides

A combination of a chimeric oligonucleotide primer and an upstream block oligonucleotide which is capable of annealing to an arbitrary portion 3' to a portion in a nucleic acid as a template to which the primer anneals was examined. First, chimeric primers for detecting *Chlamydia trachomatis* plasmid DNA, CT-BF19-3 (SEQ ID NO:6) and CT-BR23-2 (SEQ ID NO:7) were synthesized based on the nucleotide sequence of *Chlamydia trachomatis* plasmid (GenBank accession number X06707) using a DNA synthesizer. Additionally, upstream block oligonucleotides, CR-FBK (SEQ ID NO:8) and CR-RBK (SEQ ID NO:9), which have nucleotide sequences of *Chlamydia trachomatis* plasmid DNA and are capable of annealing to arbitrary portions 3' to portions in the nucleic acid as the template to which the chimeric oligonucleotide primers anneal, were synthesized. The upstream block oligonucleotides are blocked at the 3' termini by amination such that an extension reaction by the action of a DNA polymerase does not proceed. The upstream block oligonucleotides CR-FBK and CR-RBK are sense and antisense oligonucleotides, respectively.

(2) Preparation of *Chlamydia* Positive Control

A *chlamydia* positive control plasmid was prepared by PCR-amplification and purification of a 560-bp fragment corresponding to a portion of a *chlamydia* gene represented by SEQ ID NO:10, insertion of the amplified fragment into pT7 Blue T vector using DNA Ligation Kit Ver. 2 (Takara Shuzo) and transformation of *E. coli* JM109.

(3) ICAN Reaction

Reaction mixtures of final volumes of 25 μl containing 1 μl of water as a negative control or a solution containing $10^2$ to $10^6$ copies of the positive control DNA prepared in (2) above, 50 pmol each of the chimeric oligonucleotide primers and 100 pmol each of the upstream block oligonucleotides synthesized in (1) above as well as the following were prepared: 0.5 mM each of dNTPs, 32 mM Hepes-KOH buffer (pH 7.8), 100 mM potassium acetate, 4.0 mM magnesium acetate, 0.01% bovine serum albumin, 1.0% dimethyl sulfoxide, 4.375 U of Afu RNase H and 2.64 U of BcaBEST DNA polymerase (Takara Shuzo). The reaction mixtures were incubated at 60° C. for 1 hour using a thermal cycler. A group to which the upstream block oligonucleotides were not added was used as a control. After reaction, 5 μl each of the reaction mixtures was analyzed by electrophoresis on 3.0% agarose gel. The results are shown in FIG. 1. FIG. 1A represents results for the reaction system without the addition of the upstream block oligonucleotides. Lane 1: 100-bp DNA ladder marker; lane 2: negative control (water); lane 3: $10^2$ copies of the template; lane 4: $10^3$ copies of the template; lane 5: $10^4$ copies of the template; lane 6: $10^5$ copies of the template; and lane 7: $10^6$ copies of the template. FIG. 1B represents results for the reaction system with the addition of the upstream block oligonucleotides. Lane 1: 100-bp DNA ladder marker; lane 2: negative control (water); lane 3: $10^2$ copies of the template; lane 4: $10^3$ copies of the template; lane 5: $10^4$ copies of the template; lane 6: $10^5$ copies of the template; and lane 7: $10^6$ copies of the template.

As shown in FIG. 1, for the group without the addition of the upstream block oligonucleotides, amplification was observed using $10^5$ copies of the template. On the other hand, for the group with the addition of the upstream block primers, amplification was observed using $10^3$ copies of the template. Thus, the sensitivity was increased by two orders of magnitude as compared with the group without the addition. Based on these results, it was confirmed that the detection sensitivity is increased by using a combination of a chimeric oligonucleotide primer and an upstream block oligonucleotide which is capable of annealing to an arbitrary portion 3' to a portion in a nucleic acid as a template to which the chimeric oligonucleotide primer anneals.

INDUSTRIAL APPLICABILITY

The present invention provides a method for amplifying a target nucleic acid in which a region in a nucleotide sequence of a target nucleic acid that is suitable for specific amplification is amplified by a DNA synthesis reaction using a chimeric oligonucleotide primer and an upstream block oligonucleotide. The present invention further provides a method for detecting a target nucleic acid comprising a step of detecting a fragment amplified from a target nucleic acid obtained by said method for amplifying a target nucleic acid.

Sequence Listing Free Text

SEQ ID NO:2: PCR primer AfuNde for cloning a gene encoding a polypeptide having a RNaseHII activity from *Archaeoglobus fulgidus.*

SEQ ID NO:3: PCR primer AfuBam for cloning a gene encoding a polypeptide having a RNaseHII activity from *Archaeoglobus fulgidus.*

SEQ ID NO:6: Designed chimeric oligonucleotide primer designated as CT-BF19-3 to amplify a portion of *Chlamydia trachomatis* plasmid DNA. "nucleotides 20 to 22 are ribonucleotides—other nucleotides are deoxyribonucleotides."

SEQ ID NO:7: Designed chimeric oligonucleotide primer designated as CT-BR23-2 to amplify a portion of *Chlamydia trachomatis* plasmid DNA. "nucleotides 21 to 23 are ribonucleotides—other nucleotides are deoxyribonucleotides."

SEQ ID NO:8: Designed oligonucleotide designated as CR-FBK.

SEQ ID NO:9: Designed oligonucleotide designated as CR-RBK.

What is claimed is:

1. A method for amplifying a nucleic acid, the method comprising:
    (a) preparing a reaction mixture by mixing a nucleic acid as a template, a deoxyribonucleotide triphosphate, a DNA polymerase having a strand displacement activity, at least one chimeric oligonucleotide primer, at least one upstream block oligonucleotide and an RNase H, wherein the chimeric oligonucleotide primer is a chimeric oligonucleotide primer that is substantially complementary to the nucleotide sequence of the nucleic acid as the template and contains a ribonucleotide as well as at least one selected from the group consisting of a deoxyribonucleotide and a nucleotide analog, the ribonucleotide being positioned at the 3' terminus or on the 3'-terminal side of the primer, and
    wherein the upstream block oligonucleotide is substantially complementary to a nucleotide sequence 3' to a region in the nucleic acid as the template that is substantially complementary to the chimeric oligonucleotide primer, and the nucleotide at the 3' terminus of the upstream block oligonucleotide is modified such that a reaction of complementary strand extension by the action of the DNA polymerase does not take place; and
    the upstream block oligonucleotide is capable of annealing to a region 3' to a portion in the nucleic acid as the template to which the chimeric oligonucleotide primer anneals;

(b) incubating the reaction mixture for a sufficient time to generate a reaction product; and under conditions in which specific annealing of the primer and the upstream block oligonucleotide to the nucleic acid as the template, an extended strand synthesis reaction and a strand displacement reaction by the DNA polymerase, and a reaction of cleaving the extended strand by the RNase takes place.

2. The method according to claim 1, wherein the reaction mixture further contains a second chimeric oligonucleotide primer having a sequence substantially complementary to the nucleotide sequence 3' to a region to be amplified in the complementary strand of the nucleic acid as the template.

3. The method according to claim 2, wherein the reaction mixture contains a further upstream block oligonucleotide that has a sequence substantially complementary to a nucleotide sequence 3' to a region in the complementary strand of the nucleic acid as the template that has a sequence substantially complementary to the nucleotide sequence of the second chimeric oligonucleotide primer, and the nucleotide at the 3' terminus of the upstream block oligonucleotide is modified such that a reaction of complementary strand extension by the action of the DNA polymerase does not take place, and the further upstream block oligonucleotide is capable of annealing to a region 3' to a portion in the complementary strand of the nucleic acid as the template to which the second chimeric oligonucleotide primer anneals.

4. A composition for the method for amplifying a nucleic acid defined by claim 1, which contains at least one chimeric oligonucleotide primer and at least one upstream block oligonucleotide, wherein the chimeric oligonucleotide primer is a chimeric oligonucleotide primer that is substantially complementary to the nucleotide sequence of the nucleic acid as the template and contains a ribonucleotide as well as at least on member selected from the group consisting of a deoxynucleotide and a nucleotide analog, the ribonucleotide being positioned at the 3' terminus or on the 3' side of the primer, and wherein the upstream block oligonucleotide is substantially complementary to a nucleotide sequence 3' to a region in the nucleic acid as the template that is substantially complementary to the chimeric oligonucleotide primer, and the nucleotide at the 3' terminus of the upstream block oligonucleotide is modified such that a reaction of complementary strand extension by the action of the DNA polymerase does not take place, and the upstream block oligonucleotide is capable of annealing to a region 3' to a portion in the nucleic acid as the template to which the chimeric oligonucleotide primer anneals.

5. A kit for the method for amplifying a nucleic acid defined by claim 1, which contains at least one chimeric oligonucleotide primer and at least one upstream block oligonucleotide;

wherein the chimeric oligonucleotide primer is a chimeric oligonucleotide primer that is substantially complementary to the nucleotide sequence of the nucleic acid as the template and contains a ribonucleotide was well as at least one member selected from the group consisting of a deoxyribonucleotide and a nucleotide analog, the ribonucleotide being positioned at the 3' terminus or on the 3'-terminal side of the primer, and wherein the upstream block oligonucleotide is substantially complementary to a nucleotide sequence 3' to a region in the nucleid acids the template that is substancially complementary to the chimeric oligonucleotide primer, and the nucleotide at the 3' terminus of the upstream block oligonucleotide is modified such that a reaction of complementary strand extension by the action of the DNA polymerase does not take place, and the upstream block oligonucleotide is capable of annealing to a region 3' to a portion in the nucleic acid as the template to which the chimeric oligonucleotide primer anneals.

6. A method for detecting a target nucleic acid, the method comprising:

(a) amplifying a target nucleic acid by the method for amplifying a nucleic acid defined by claim 1; and (b) detecting a target nucleic acid amplified in the previous step.

* * * * *

SEQUENCE LISTING

```
<160> NUMBER OF SEQ ID NOS: 10

<210> SEQ ID NO 1
<211> LENGTH: 626
<212> TYPE: DNA
<213> ORGANISM: Archaeoglobus fulgidus

<400> SEQUENCE: 1
atgaaggcag gcatcgatga ggctggaaag ggctgcgtca tcggcccact ggttgttgca     60
ggagtggctt gcagcgatga ggataggctg agaaagcttg gtgtgaaaga ctccaaaaag    120
ctaagtcagg ggaggagaga ggaactagcc gaggaaataa ggaaaatctg cagaacggag    180
```

-continued

```
gttttgaaag tttctcccga aaatctcgac gaaaggatgg ctgctaaaac cataaacgag      240
attttgaagg agtgctacgc tgaaataatt ctcaggctga agccggaaat tgcttatgtt      300
gacagtcctg atgtgattcc cgagagactt cgagggagc ttgaggagat tacggggttg       360
agagttgtgg ccgagcacaa ggcggacgag aagtatcccc tggtagctgc ggcttcaatc      420
atcgcaaagg tggaaaggga gcgggagatt gagaggctga agaaaaaatt cggggatttc      480
ggcagcggct atgcgagcga tccgaggaca agagaagtgc tgaaggagtg gatagcttca     540
ggcagaattc cgagctgcgt gagaatgcgc tggaagacgg tgtcaaatct gaggcagaag      600
acgcttgacg atttctaaac gaaacc                                           626
```

<210> SEQ ID NO 2
<211> LENGTH: 30
<212> TYPE: DNA
<213> ORGANISM: Artificial
<220> FEATURE:
<223> OTHER INFORMATION: Synthetic - PCR primer AfuNde for cloning a
      gene encoding a
      polypeptide having a RNaseHII activity from Archaeoglobus
      fulgidus

<400> SEQUENCE: 2

```
aagctgggtt tcatatgaag gcaggcatcg                                       30
```

<210> SEQ ID NO 3
<211> LENGTH: 30
<212> TYPE: DNA
<213> ORGANISM: Artificial
<220> FEATURE:
<223> OTHER INFORMATION: Synthetic - PCR primer AfuBam for cloning a
      gene encoding a
      polypeptide having a RNaseHII activity from Archaeoglobus
      fulgidus

<400> SEQUENCE: 3

```
tggtaataac ggatccgttt agaaatcgtc                                       30
```

<210> SEQ ID NO 4
<211> LENGTH: 638
<212> TYPE: DNA
<213> ORGANISM: Archaeoglobus fulgidus

<400> SEQUENCE: 4

```
catatgaagg caggcatcga tgaggctgga aagggctgcg tcatcggccc actggttgtt      60
gcaggagtgg cttgcagcga tgaggatagg ctgagaaagc ttggtgtgaa agactccaaa     120 agctaagtc aggggaggag agaggaacta gccgaggaaa taggaaaat ctgcagaacg        180 gaggttttga agtttctcc cgaaaatctc gacgaaagga tggctgctaa aaccataaac      240
gagattttga aggagtgcta cgctgaaata attctcaggc tgaagccgga aattgcttat      300
gttgacagtc ctgatgtgat tcccgagaga ctttcgaggg agcttgagga gattacgggg      360
ttgagagttg tggccgagca caaggcggac gagaagtatc ccctggtagc tgcggcttca      420
atcatcgcaa aggtggaaag ggagcggag attgagaggc tgaaagaaaa attcggggat     480
ttcggcagcg gctatgcgag cgatccgagg acaagagaag tgctgaagga gtggatagct      540
tcaggcagaa ttccgagctg cgtgagaatg cgctggaaga cggtgtcaaa tctgaggcag      600
aagacgcttg acgatttcta aacggatccc cgggtacc                              638
```

<210> SEQ ID NO 5
<211> LENGTH: 205

```
<212> TYPE: PRT
<213> ORGANISM: Archaeoglobus fulgidus

<400> SEQUENCE: 5

Met Lys Ala Gly Ile Asp Glu Ala Gly Lys Gly Cys Val Ile Gly Pro
1               5                   10                  15

Leu Val Val Ala Gly Val Ala Cys Ser Asp Glu Asp Arg Leu Arg Lys
                20                  25                  30

Leu Gly Val Lys Asp Ser Lys Lys Leu Ser Gln Gly Arg Arg Glu Glu
            35                  40                  45

Leu Ala Glu Glu Ile Arg Lys Ile Cys Arg Thr Glu Val Leu Lys Val
50                  55                  60

Ser Pro Glu Asn Leu Asp Glu Arg Met Ala Ala Lys Thr Ile Asn Glu
65                  70                  75                  80

Ile Leu Lys Glu Cys Tyr Ala Glu Ile Ile Leu Arg Leu Lys Pro Glu
                85                  90                  95

Ile Ala Tyr Val Asp Ser Pro Asp Val Ile Pro Glu Arg Leu Ser Arg
            100                 105                 110

Glu Leu Glu Glu Ile Thr Gly Leu Arg Val Val Ala Glu His Lys Ala
            115                 120                 125

Asp Glu Lys Tyr Pro Leu Val Ala Ala Ser Ile Ile Ala Lys Val
            130                 135                 140

Glu Arg Glu Arg Glu Ile Glu Arg Leu Lys Glu Lys Phe Gly Asp Phe
145                 150                 155                 160

Gly Ser Gly Tyr Ala Ser Asp Pro Arg Thr Arg Glu Val Leu Lys Glu
                165                 170                 175

Trp Ile Ala Ser Gly Arg Ile Pro Ser Cys Val Arg Met Arg Trp Lys
            180                 185                 190

Thr Val Ser Asn Leu Arg Gln Lys Thr Leu Asp Asp Phe
            195                 200                 205

<210> SEQ ID NO 6
<211> LENGTH: 22
<212> TYPE: DNA
<213> ORGANISM: Artificial
<220> FEATURE:
<223> OTHER INFORMATION: Synthetic - Designed chimeric oligonucleotide
      primer designated
      as CT-BF19-3 to amplify a portion of Chlamydia trachomatis
      plasmid DNA.
<220> FEATURE:
<221> NAME/KEY: misc_feature
<222> LOCATION: (20)..(22)
<223> OTHER INFORMATION: Nucleotides 20 to 22 are ribonucleotides-other
      nucleotides are
      deoxyribonucleotides

<400> SEQUENCE: 6
catacggttt tcctcgatga uu                                          22

<210> SEQ ID NO 7
<211> LENGTH: 23
<212> TYPE: DNA
<213> ORGANISM: Artificial
<220> FEATURE:
<223> OTHER INFORMATION: Synthetic - Designed chimeric oligonucleotide
      primer designated
      as CT-BR23-2 to amplify a portion of Chlamydia trachomatis
      plasmid DNA.
<220> FEATURE:
<221> NAME/KEY: misc_feature
<222> LOCATION: (21)..(23)
<223> OTHER INFORMATION: Nucleotides 21 to 23 are ribonucleotides-other
```

-continued

```
           nucleotides are
           deoxyribonucleotides.

<400> SEQUENCE: 7
gatctacgca atggattttc auu                                        23

<210> SEQ ID NO 8
<211> LENGTH: 20
<212> TYPE: DNA
<213> ORGANISM: Artificial
<220> FEATURE:
<223> OTHER INFORMATION: Synthetic - Designed oligonucleotide designated
      as CR-FBK

<400> SEQUENCE: 8
gacaagctta gatccgtttc                                            20

<210> SEQ ID NO 9
<211> LENGTH: 20
<212> TYPE: DNA
<213> ORGANISM: Artificial
<220> FEATURE:
<223> OTHER INFORMATION: Synthetic - Designed oligonucleotide designated
      as CR-RBK

<400> SEQUENCE: 9
cgctcaagca atagaaacgg                                            20

<210> SEQ ID NO 10
<211> LENGTH: 560
<212> TYPE: DNA
<213> ORGANISM: Chlamydia trachomatis

<400> SEQUENCE: 10
atgcgttgtt aggtaaagct ctgatatttg aagactctac tgagtatatt ctgaggcagc    60
ttgctaatta tgagtttaag tgttctcatc ataaaaacat attcatagta tttaaatact   120
taaaagacaa tggattacct ataactgtag actcggcttg ggaagagctt ttgcggcgtc   180
gtatcaaaga tatggacaaa tcgtatctcg ggttaatgtt gcatgatgct ttatcaaatg   240
acaagcttag atccgtttct catacggttt tcctcgatga tttgagcgtg tgtagcgctg   300
aagaaaattt gagtaatttc attttccgct cgtttaatga gtacaatgaa aatccattgc   360
gtagatctcc gtttctattg cttgagcgta taaagggaag gcttgacagt gctatagcaa   420
agactttttc tattcgcagc gctagaggcc ggtctattta tgatatattc tcacagtcag   480
aaattggagt gctggctcgt ataaaaaaaa gacgagcaac gttctctgag aatcaaaatt   540
ctttctttga tgccttccca                                              560
```